United States Patent [19]

Hunsucker et al.

[11] 4,088,817

[45] May 9, 1978

[54] PROCESS FOR THE PRODUCTION OF NON-LACHRYMATORY NITRO AMINES

[75] Inventors: Jerry Hoyt Hunsucker; Robert Wayne Shelton, both of Terre Haute, Ind.

[73] Assignee: IMC Chemical Group, Inc., Terre Haute, Ind.

[21] Appl. No.: 763,272

[22] Filed: Jan. 27, 1977

[51] Int. Cl.$^2$ ............................................. C07D 295/06
[52] U.S. Cl. ..................................... 544/162; 544/86; 424/248.4
[58] Field of Search ............................ 260/247, 246 B; 544/162, 86

[56] References Cited

U.S. PATENT DOCUMENTS 2,474,791   6/1949   Senkus ................................. 260/247

Primary Examiner—Henry R. Jiles
Assistant Examiner—R. W. Ramsuer
Attorney, Agent, or Firm—Robert H. Dewey; Roger A. Williams

[57] ABSTRACT

An improvement in the process for the production of P-1487 from the reaction of 1-nitropropane, 37% formaldehyde and morpholine, the improvement comprising mixing 1-nitropropane and 37% formaldehyde at a temperature of 40°–42° C, adding morpholine maintaining the temperature at 40°–42° C, holding the mixture for two hours at 40°–42° C, cooling to allow layer separation, separating the upper oil layer and concentrating the oil layer to P-1487 by removing excess water.

1 Claim, No Drawings

PROCESS FOR THE PRODUCTION OF NON-LACHRYMATORY NITRO AMINES

BACKGROUND OF THE INVENTION

This invention relates to an improvement in the process for the production of a mixture of 80–90% 4-(2-nitrobutyl)morpholine and 3–10% 4,4'-(2-nitro-2-ethyltrimethylene)dimorpholine, hereinafter referred to as P-1487.

More particularly, this invention relates to an improvement in the process for the production of P-1487 from the reactants: 1-nitropropane, morpholine and formaldehyde to produce a non-lachrymatory P-1487 product.

The prior known processes for the production of nitro amines, Senkus, U.S. Pat. Nos. 2,474,791 and 2,447,821 teach the production of nitro amines from the reaction of a nitroalcohol and a cyclic secondary amine (2-nitro-2-methyl-1-propanol and morpholine), or a primary amine in which the N substituents are cyclic groups. A second process taught by Senkus in the above patents is the reaction of formaldehyde with a cyclic secondary amine (or primary amine) which, in turn, is reacted with a nitroparaffin. Senkus does not, however, directly teach the reaction of combining the formaldehyde with the nitroparaffin to produce a nitroalcohol which is subsequently reacted with the amine to produce a nitro amine.

A mixture of 80–90% of 4-(2-nitrobutyl)morpholine and 3–10% of 4,4'-(2-nitro-2-ethyltrimethylene)dimorpholine, hereinafter referred to as P-1487, is a known pesticide available commercially. The utility of the mixture as a pesticide is hampered by the high lachrymatory properties of the mixture that appeared to be inherent in the mixture.

The current industrial method of producing P-1487 is well known in the art. In this current industrial method, formaldehyde is reacted with a nitroparaffin at a temperature of between 60°–70° C then the amine, e.g. morpholine, is added maintaining the temperature between 60°–70° C. The present method produces lachrymatory high nitro amine P-1487 product. The formation of the lachrymators was first thought to be due to the production of nitroolefins, which are severe eye irritants. Additional amine (e.g. morpholine) was added to prevent the formation of the nitroolefins or to react with the lachrymators as they were formed to form non-objectionable products. However, the eye irritation and formation of lachrymators remained.

SUMMARY OF THE INVENTION

It is an object of this invention to provide an improvement in the process for the production of P-1487.

Another object of this invention is to provide an improvement in the process for the production of P-1487 from the reaction of 1-nitropropane, morpholine and formaldehyde to produce a non-lachrymatory P-1487 product.

Other objects of this invention will be apparent to those skilled in the art from the disclosure herein.

An improvement has been found in the process for the production of P-1487 from the reaction of 1-nitropropane, 37% formaldehyde and morpholine, the improvement comprising producing a non-lachrymatory P-1487 product by mixing 1-nitropropane and formaldehyde at a temperature of 42° C, adding morpholine under isothermal conditions, holding the reaction mixture at 42° C for a two-hour period, cooling and separating the layers formed, and concentrating the oil layer to P-1487 by removing excess water.

DETAILED DISCUSSION

The improved process of this invention produces a product that is non-lachrymatory. The process of this invention involves the reaction of 1-nitropropane, 37% formaldehyde and morpholine (tetrahydro-1,4-oxazine) to form P-1487, a mixture containing from about 80–90% 4-(2-nitrobutyl)morpholine and from about 3–10% 4,4'-(2-nitro-2-ethyltrimethylene)dimorpholine. The formation of the two products occurs simultaneously with the dimorpholine product reaction being limited by the availability of morpholine and formaldehyde. In the presence of water, the 4,4'-(2-nitro-2-ethyltrimethylene)dimorpholine reaction is reversible and follows the reaction:

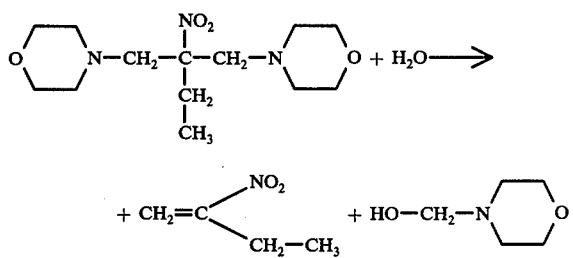

The 2-nitro-1-butene formed is a known highly lachrymatory material. The process described by this invention limits the formation of 2-nitro-1-butene by the above reaction and thereby decreases the lachrymatory properties of the P-1487 product.

In the process of this invention, 1-nitropropane and 37% formaldehyde are charged to a reaction vessel equipped with an agitator and means for heating and cooling. The ratio of reactants is 1.22 moles of morpholine and 1.20 moles of formaldehyde per 1.00 moles of 1-nitropropane. The formaldehyde and 1-nitropropane are mixed in the reactor and heated to 35°–45° C. A temperature of between 40°–42° C is preferred.

Morpholine is added to mixture with constant agitation and maintenance of the temperature in the 35°–45° C range. Temperatures higher than 45° C produce nitro compounds that are not completely substituted and give rise to a lachrymatory product. Temperatures below 35° C generally do not drive the reaction. A temperature of between 40°–42° C is preferred for the addition of the morpholine, this range is sufficient to initiate the reaction, yet does not promote the formation of lachrymators in the P-1487 product. The morpholine is added to the well-agitated mixture with cooling to maintain the temperature of the mixture in the preferred 40°–42° C. The rate of addition of morpholine is determined by the cooling capacity of the equipment. Generally, an addition period of from three to six hours is adequate to complete the addition of morpholine with the least amount of temperature fluctuation. The reaction is completed by holding the reactants for a two-hour period at the temperature of 40°–42° C following the addition of the morpholine.

Following the holding period, the reaction mixture is cooled to less than 30° C and agitation is discontinued. The reaction mixture is allowed to stand for eight hours for separation of the layers. The lower oil layer, containing the P-1487 product, is removed and held for concentration. The upper water layer is discarded.

The oil layer is concentrated, stripped of water, by heating to a temperature of 42° C at 15–20 mm Hg for one hour. The water stripped from the oil layer is discarded. The oil is cooled to less than 30° C. The oil layer is the P-1487 product containing from about 80–90% 4-(2-nitrobutyl)morpholine and from about 3–10% 4,4'-(2-ethyl-trimethylene)dimorpholine. The P-1487 product formed exhibits no significant eye irritation properties.

The process of this invention will be better understood with reference to the following examples. It is understood that these examples are intended for illustration only and it is not intended that the invention be limited thereby.

EXAMPLE 1

The materials were pre-measured by weighing for accurate ratioing in the proportions of 1.22 moles of morpholine and 1.20 moles of formaldehyde per 1.00 moles of 1-nitropropane. To a reaction vessel equipped with an agitator and a heating and cooling means were charged 1052.6 lbs of formaldehyde (100%), 1451.0 lbs of water and 341.4 lbs of methanol to give a 37% solution of formaldehyde. To the vessel was charged 2603 lbs of 1-nitropropane. The formaldehyde and 1-nitropropane are mixed and heated to 40°–42° C. Morpholine, 3105 lbs, was fed into the well-agitated mixture of 1-nitropropane and 37% formaldehyde with cooling to maintain the temperature of the liquid at 40°–42° C. The rate of addition of morpholine was determined by the cooling capacity of the reaction vessel, generally a 3 to 6 hour period. Following the morpholine addition, the reaction was driven to completion by holding for a two-hour period at a temperature of 41° ± 1° C liquid temperature by the use of external heat, supplied by a heating fluid of 43° ± 2° C. The reaction mixture was then cooled to less than 30° C and agitation discontinued. The reaction mixture was allowed to stand for 8 hours to promote separation into layers. The lower oil layer, containing the P-1487 product, was removed and held for concentration. The water layer was discarded. The oil layer was concentrated, stripped of water, by heating to 42° C, liquid temperature, at 15–20 mm Hg for one hour.

The product contained 88.95% of 4-(2-nitrobutyl)-morpholine and 3.85% 4,4'-(2-nitro-2-ethyltrimethylene)-dimorpholine. The P-1487 product produced when screened for eye irritation properties was found to be non-lachrymatory.

EXAMPLES 2–13

The experiment of Example 1 was repeated in all essential details. The product produced was shown to be non-lachrymatory. The results of the examples are given in the table.

TABLE

| | Gas Chromatographic Analysis of Nitro Amine Product | | | | | | | |
|---|---|---|---|---|---|---|---|---|
| Example | $H_2O$ | 2-NP | 1-NP | Morpholine | 2-Nitro-1-Butanol | 4-(2-Methyl-2-nitropropyl) Morpholine | 4-(2-Nitrobutyl) Morpholine | Unknown 4-(2-Hydroxymethyl-2-nitrobutyl) Morpholine[3] | 4,4'-(2-Nitro-2-ethyltrimethylene) Dimorpholine |
| 1 | 0.20 | -2.26-[1] | | 1.61 | 0.73 | 0.35 | 88.95 | 2.05 | 3.85 |
| 2 | 0.20 | -2.78- | | 3.86 | 0.76 | 1.38 | 85.73 | 1.50 | 3.78 |
| 3 | 0.32 | 0.79 | 2.34 | 2.67 | T[2] | 0.86 | 87.30 | 1.81 | 3.84 |
| 4 | 0.31 | 0.68 | 2.09 | 2.25 | T | 0.80 | 88.19 | 1.76 | 3.85 |
| 5 | 0.40 | -1.07- | | 4.26 | 0.47 | 1.40 | 82.52 | 2.22 | 7.48 |
| 6 | 0.32 | 0.47 | 2.46 | 2.77 | 0.76 | Not Resolved | 86.49 | 2.45 | 4.08 |
| 7 | 0.19 | 0.49 | 1.77 | 2.46 | T | Not Resolved | 87.93 | 2.25 | 4.69 |
| 8 | T | 0.97 | 1.64 | 2.65 | T | Not Resolved | 82.05 | 1.23 | 5.36 |
| 9 | T | -1.84- | | 3.08 | 0.49 | 1.12 | 85.37 | 1.70 | 5.62 |
| 10 | 0.23 | 0.34 | 1.68 | 2.25 | T | Not Resolved | 88.72 | 2.46 | 4.29 |
| 11 | 0.11 | 0.33 | 1.20 | 3.47 | 0.63 | Not Resolved | 87.24 | 2.53 | 4.46 |
| 12 | 0.19 | 0.29 | 1.24 | 2.35 | 0.56 | Not Resolved | 87.65 | 2.35 | 5.09 |
| 13 | 0.17 | 0.58 | 1.08 | 2.95 | T | 1.62 | 84.51 | 1.84 | 6.66 |

[1]Integrated as one peak.
[2]Trace amount present below integration limits.
[3]Believed to be this compound.

We claim:

1. An improvement in the process for the production of P-1487 from the reaction of 1-nitropropane, 37% formaldehyde and morpholine the improvement comprising mixing 1-nitropropane and 37% formaldehyde at a temperature of 40°–42° C, adding morpholine under isothermal conditions, holding the mixture at 40°–42° C for a two hour period following the addition of morpholine, cooling the reaction mixture to less than 30° C, separating the oil layer, and concentrating the oil layer to P-1487 by removing excess water.

* * * * *